US005123915A

United States Patent [19]

Miller et al.

[11] Patent Number: 5,123,915

[45] Date of Patent: Jun. 23, 1992

[54] MEDICATED PACIFIER

[76] Inventors: Lawrence E. Miller; Jeffrey Miller, both of P.O. Box 557, Oldwick, N.J. 08858

[21] Appl. No.: 515,614

[22] Filed: Apr. 27, 1990

[51] Int. Cl.[5] ........................ A61M 31/00; A61J 7/00; A61J 17/00

[52] U.S. Cl. .................................... 606/234; 606/236; 604/77

[58] Field of Search ................ 604/77; 215/11.1, 11.2, 215/11.3, 11.4, 11.5, 11.6; 606/234, 235, 236

[56] References Cited

U.S. PATENT DOCUMENTS

| | | | |
|---|---|---|---|
| 404,950 | 6/1889 | Barnes . | |
| 735,707 | 8/1903 | Cantwell | 215/11.1 |
| 745,920 | 12/1903 | Spencer . | |
| 779,749 | 1/1905 | Tinling | 215/11.1 |
| 1,070,516 | 8/1913 | O'Brien | 215/11.1 |
| 3,875,940 | 4/1975 | Beuther | 604/77 |
| 4,192,307 | 3/1980 | Baer | 128/252 |
| 4,488,551 | 12/1984 | Connelly | 128/360 |
| 4,784,641 | 11/1988 | White | 604/77 |

FOREIGN PATENT DOCUMENTS

| | | | |
|---|---|---|---|
| 0544571 | 2/1956 | Belgium | 606/236 |
| 3820291 | 12/1989 | Fed. Rep. of Germany | 215/11.5 |
| 0014933 | of 1892 | United Kingdom | 606/236 |
| 0536196 | 5/1941 | United Kingdom | 606/236 |
| 2057274 | 4/1981 | United Kingdom | 606/236 |

*Primary Examiner*—Stephen C. Pellegrino
*Assistant Examiner*—Glenn K. Dawson
*Attorney, Agent, or Firm*—Mathews, Woodbridge & Collins

[57] ABSTRACT

The present invention pertains to a device for the oral administration of a medication. The device comprises a pierced nipple having a nipple chamber and an open base, a medication reservoir having an outer wall member defining a reservoir chamber, a first end opening into the reservoir chamber, and a closable second end opening into the reservoir chamber. There are means to connect the reservoir to the base of the nipple in fluid-tight relationship with the nipple chamber communicating with the reservoir chamber through the open base. There are closing means for sealing the second end of the reservoir.

14 Claims, 3 Drawing Sheets

MEDICATED PACIFIER

FIELD OF INVENTION

The present invention is in the field of medicine dispensers; and more particularly pertains to a pacifier for dispensing medicine.

DESCRIPTION OF THE RELATED ART

Dispensing medication to infants by mouth has always been a particular problem for parents as well as medical practitioners. Attempts to use droppers or spoonfuls of liquid usually result in the waste and spillage of more medicine than the infant actually ingests since infants are generally noncooperative. This can create a situation in which important and sometimes critical medications are given in incorrect dosages or maybe not at all. In the past it was only possible to orally dispense medications to infants which were in a purely liquid formulation.

Barnes, U.S. Pat. No. 404,950 describes a medicine dispenser for infants which consists of a rubber nipple connected to a rubber bulb. The medicine is drawn into the nipple portion of the dispenser after air has been expressed from the bulb thereby creating a vacuum. The use of this device is limited to liquid preparations of medications.

Spencer, U.S. Pat. No. 745,920 describes a baby comforter in which a piece of cotton soaked with a nutrient liquid or a medication is placed into a pacifier-like device for inserting into the mouth of an infant. The device is also constructed so as to minimize the amount of air that the baby intakes as a result of comforter use. The use of this device in dispensing medications in which the dosage is important is not possible nor practical and its use is limited to liquids only.

Baer, U.S. Pat. No. 4,192,307 describes a sweet-dispensing pacifier. The perforated nipple portion may be removed from the pacifier in order to insert a sweet such as a pellet of candy or frozen fruit juice. This invention has limited use in dispensing medications since only solid substances which dissolve when contacted with a liquid may be inserted into the nipple chamber.

Connelly, U.S. Pat. No. 4,488,551 is directed to a pacifier which has a means for controlling the flow of a liquid. The interior chamber of the nipple is filled with an absorbent material which acts as a barrier to restrict the flow of fluid therein. This device is not for use in delivering medication.

White, U.S. Pat. No. 4,784,641 describes a syringe and a method for the oral administration of fluidic material to a patient. The syringe is equipped with a nipple-like cannula at the dispensing end to provide a surface for patients to suck on. The syringe must be continuously held by the individual dispensing the medicine as its use requires their active participation. The device is also not suitable for small infants who might reject the syringe from their mouths.

SUMMARY OF THE INVENTION

In accordance with one embodiment, the present invention pertains to a device for the oral administration of a medication. The device comprises a pierced nipple having a nipple chamber and an open base and a medication reservoir having an outer wall member defining a reservoir chamber, a first end opening into the reservoir chamber, and a closable second end opening into the reservoir chamber. Means, as for example, a threaded collar, connect the reservoir to the base of the nipple in fluid-tight relationship. The nipple chamber communicates with the reservoir chamber through the open base, and for example a strainer or a hollow piercing means. Closing means, as for example a "child-safety" cap or a "shutter-cap" are operable to seal the second end of the reservoir. The device further comprises a mouth guard which is fixed to the device.

In accordance with another embodiment, the present invention pertains to a method for the oral administration of a medication to a patient with a device comprising a pierced nipple having a nipple chamber and an open base, a medication reservoir having an outer wall member defining a hollow reservoir chamber, a first end opening into the reservoir chamber and communicating with the nipple chamber, and a closable second end opening into the reservoir chamber, means disposed on the first end for firmly engaging the base of the nipple in fluid-tight relationship, and closing means operable to seal the second end of the reservoir. The method comprises the steps of adding a medication formulation to the reservoir, and administering the medication to the patient through the nipple.

In the past, oral medication dispensers have been limited to use with liquid formulations of medications almost exclusively. Dosages have sometimes been inexact due to the inexperience of the individual responsible for the patients care, as for example, a new parent, etc. The present invention can provide oral administration of medications which come in various more convenient, less wasteful and thereby more accurate dosage formulations.

BRIEF DESCRIPTION OF THE DRAWINGS

Structural elements in FIGS. 4–7 which correspond to those in FIGS. 1–3 have been assigned the corresponding reference number plus 100.

Structural elements in FIGS. 8–11 which correspond to those in FIGS. 1–3 have been assigned the corresponding reference number plus 200.

DETAILED DESCRIPTION

Figure 1:
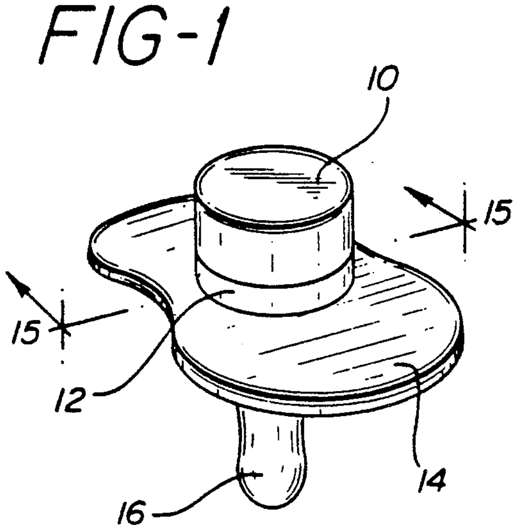
FIG. 1 is a view in perspective of an embodiment of the device of the present invention.
Figure 2:
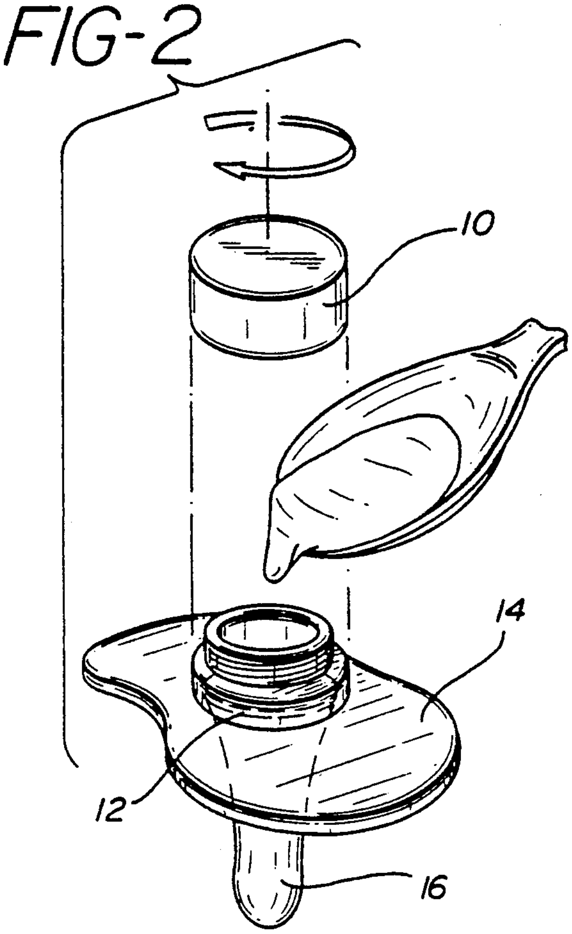
FIG. 2 is an exploded view of the embodiment of FIG. 1.
Figure 3:
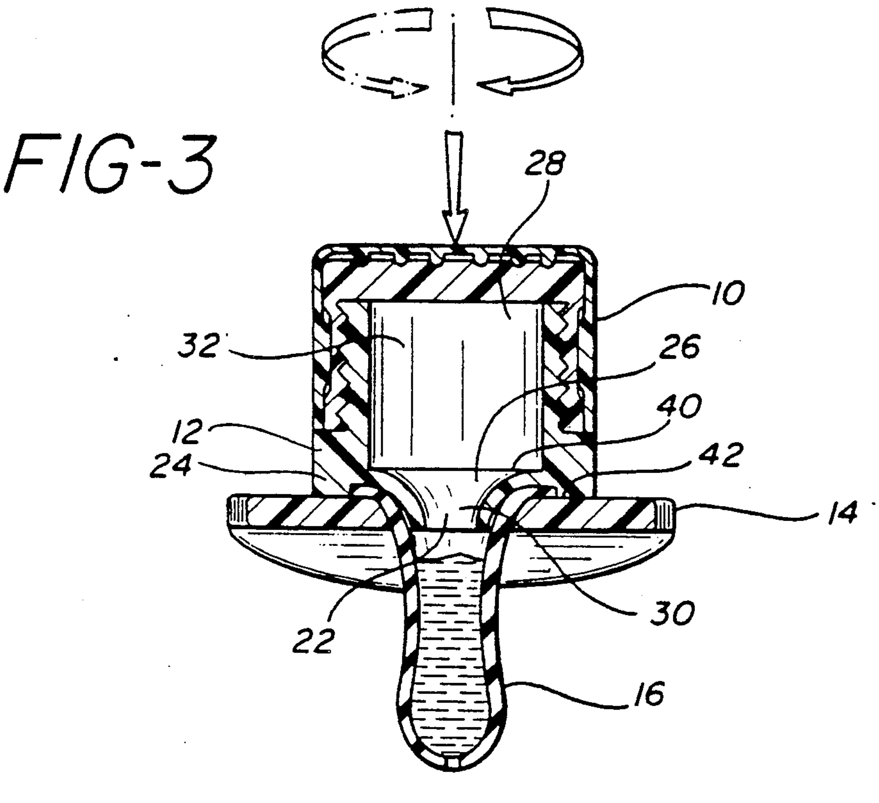
FIG. 3 is a sectional view of FIG. 1 along 3—3.

Turning now to FIGS. 1–3 of the drawings, there is illustrated a device for the oral administration of a medication formulation in accordance with the present invention.

The device comprises a nipple 16 having nipple chamber 20, and a reservoir 12 having a reservoir chamber 32. The nipple 16 is sealingly connected to reservoir 12. Nipple chamber 20 communicates with reservoir chamber 32. There is a suitable means to introduce medicine into reservoir chamber 32.

More particularly, nipple 12 has an open base 22 to nipple chamber 20. The nipple 16 is pierced with at least one hole preferably at the tip. The base 22 is sealingly connected to reservoir 12. The nipple is preferably constructed from any of a number of rubbers or rubberized plastics which are traditionally used in the art. The reservoir, mouth guard and closing means are preferably constructed from any of a number of liquid impervious plastics, acrylics, or other polymers which are nontoxic.

Medication reservoir 12 has outer wall member 24 defining reservoir chamber 32, first end 26 opening into reservoir chamber 32, and second end 28. There is a closable opening into reservoir chamber 32 preferably located at second end 28. Reservoir 12 is connected by suitable connecting means 30 to base 22 of nipple 16 in fluid-tight relationship with the nipple chamber 20 communicating with reservoir chamber 32.

A useful engaging means 30 is illustrated in FIG. 3. In this embodiment the nipple 16 has a circumferential nipple flange 40 at base 22. The base is sealingly forced against the reservoir 12 at the first end 26 around the opening in the first end. The circumferential nipple flange 40 is forced against the first end 26 of reservoir 12 by mouth guard 14 which is connected to reservoir 12. Other useful connecting means 30 can be used such as the means illustrated in the various embodiments of the present invention presented herein.

Mouth guard 14 is fixed to the device in a position which is preferably proximal to first end 26 of reservoir 12 and distal to closable second end 28 of reservoir 12. Preferably the mouth guard is located between the nipple 16 and the reservoir 14.

The mouth guard in the embodiment illustrated in FIGS. 1–3 is connected to the first end 26 of the reservoir at interface 42. The connection can be by suitable means to connect opposing plastic surfaces such as adhesives or heat sealing.

Closing means 10, as for example as shown here a screw cap, is operable to seal second end 28 of reservoir 12. Preferably closing means 10 is any one of a number of "child safety" caps which provide a fluid tight seal between first end 26 of reservoir 12 and the cap. "Child-safety" caps are well known in the pharmacological arts. The use of a "child-safety" cap as a means for closing the second end of the device provides the care giver with the opportunity to leave the device with the patient or infant unattended.

The opening in the closable second end 28 is of dimensions sufficient to receive a medication formulation, as for example, from an eyedropper, a spoon, or a semisolid or solid lozenge.

In use, closing means 10 is removed, a formulation of medication is introduced into reservoir 12, and closing means 10 is replaced. In those instances when a lozenge formulation is used, the medication introduction is followed by the introduction of a liquid which acts to dissolve the lozenge prior to use.

Figure 4:
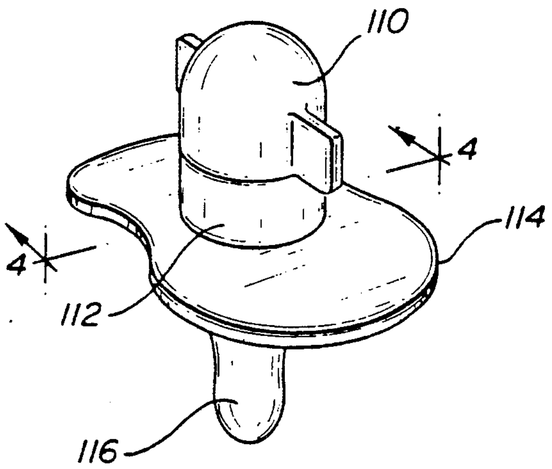
FIG. 4 is a view in perspective of a preferred embodiment of the present invention.
Figure 5:
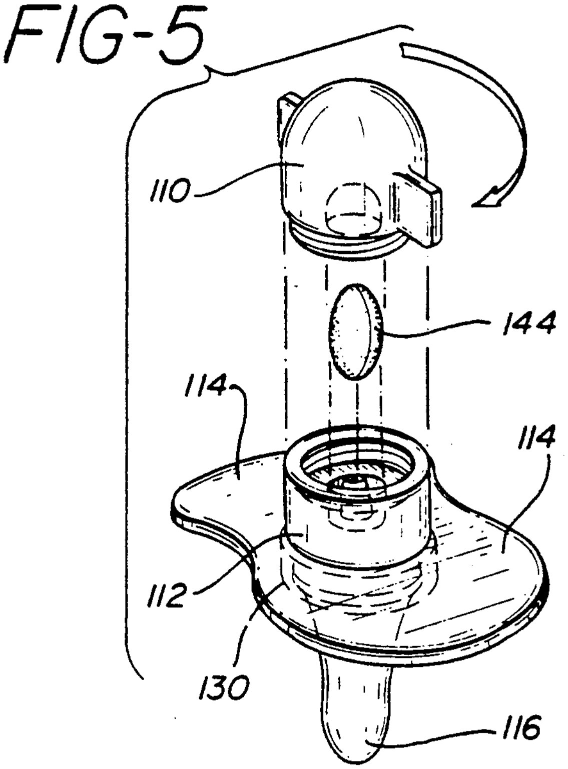
FIG. 5 is an exploded view of the embodiment of FIG. 4.
Figure 6:
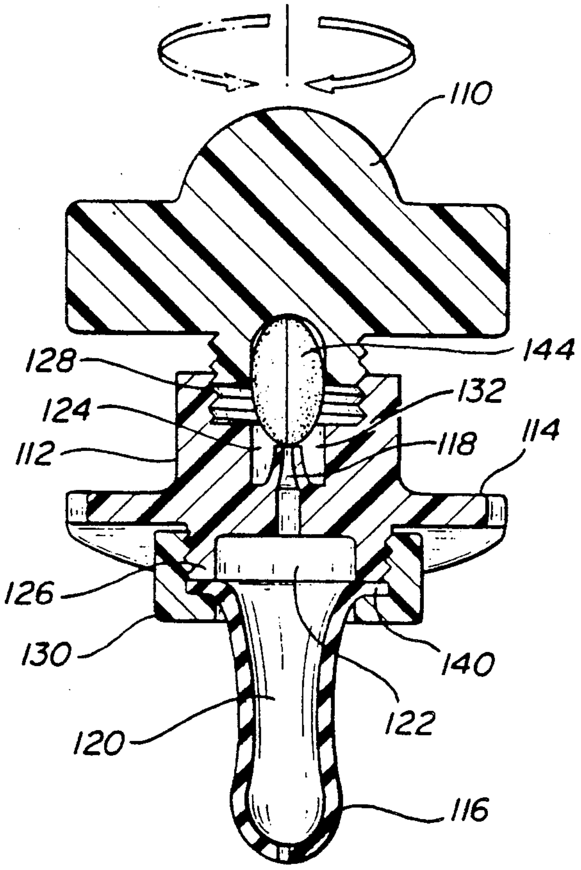
FIG. 6 is a sectional view along A—A of the embodiment of FIG. 4 with the cap in the open position.
Figure 7:
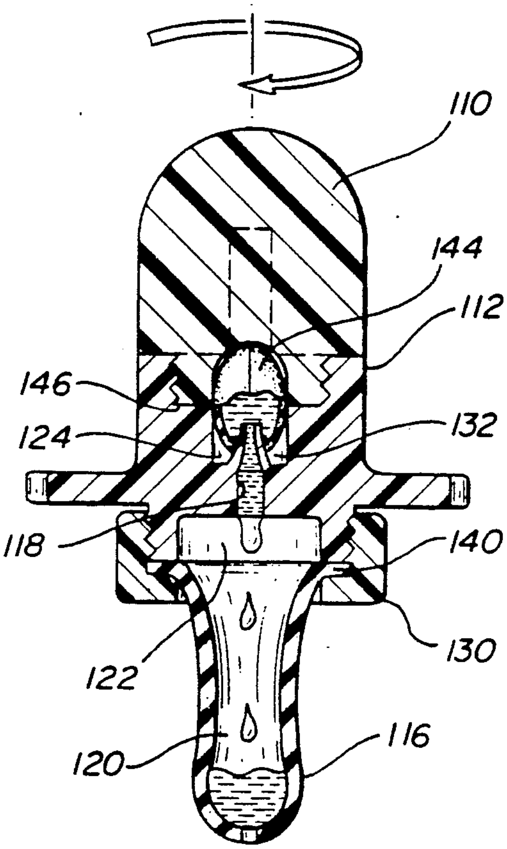
FIG. 7 is a sectional view of the embodiment in FIG. 4 along A—A with the cap in the closed position.
Figure 8:
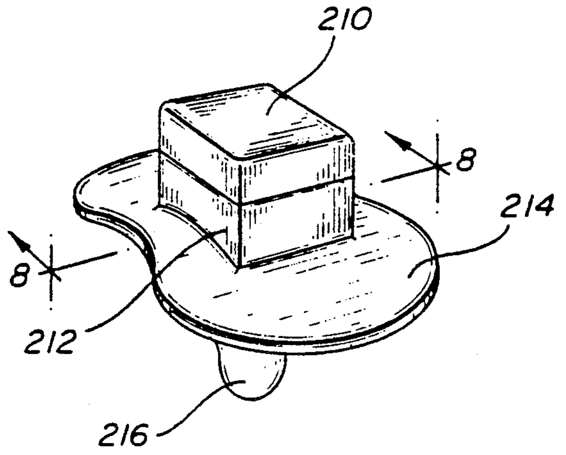
FIG. 8 is a view in perspective of a further embodiment of the present invention.
Figure 9:
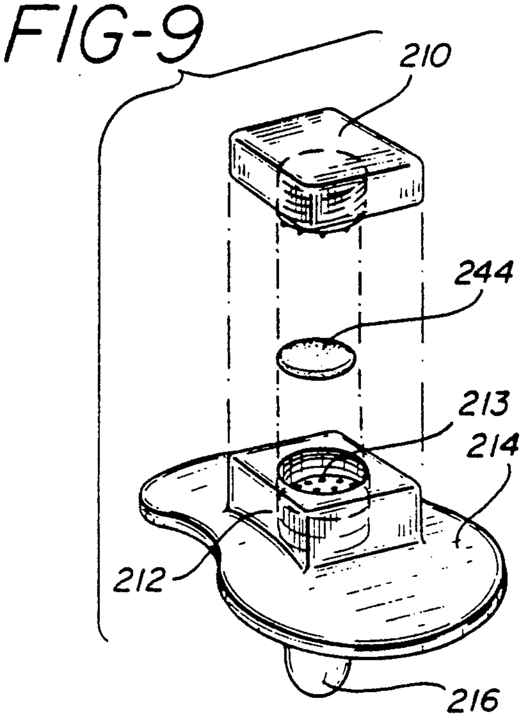
FIG. 9 is an exploded view of the embodiment of FIG. 8.
Figure 10:
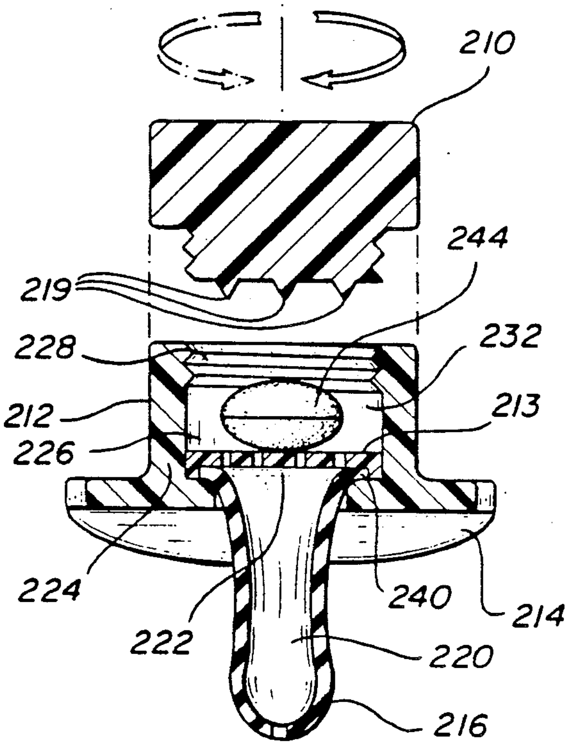
FIG. 10 is sectional view of the embodiment of FIG. 8 along B—B with the cap in the open position.
Figure 11:
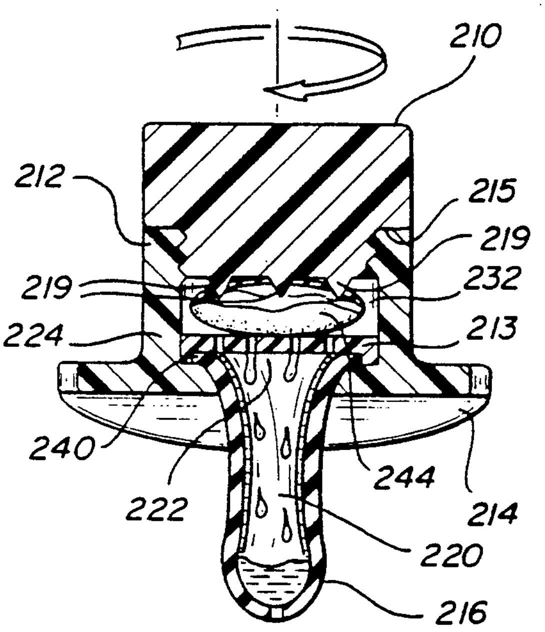
FIG. 11 is a sectional view of the embodiment of FIG. 8 along B—B with the cap in the closed position.

Referring now to FIGS. 4–6 wherein similar reference characters designate corresponding parts throughout the several views, a preferred embodiment of the present invention is illustrated.

Pierced nipple 116 has nipple chamber 120 and open base 122 with circumferential nipple flange 140. Medication reservoir 112 has outer wall member 124 defining reservoir chamber 132 having a volume fixed to be less than that of a formulation of a medication, as for example a gelcap 144. There is a first end 126 having an opening from reservoir chamber 132, and second end 128. Closable second end 128 is of sufficient dimensions to receive a medication formulation, here, a gelcap. First end 126 communicates with nipple chamber 120 through hollow piercing means 118 which is fixed to first end 126 and protruding into reservoir chamber 132.

There is a means 130, here shown as a screw on collar, for firmly engaging the flange 140 of nipple 116 in fluid-tight relationship with first end 126. There is a closing means to sealingly close second end 128 of reservoir 112. The closing means has associated therewith a means to extend into and decrease the volume of reservoir chamber 132 as the closing means closes the second end 112. The closing means can be a cap 110 which screws into the second end 128 of reservoir 112. Preferably a seal is formed at the interface 146 of contacting surface between closing means 110 and closable second end 128 when the cap 110 is in a closed position. A mouth guard 114 is fixed to the device at a position which is preferably proximal to first end 126 of reservoir 112 and distal to closable second end 128 of reservoir 112. The mouth guard 114 is a commonly molded extension near the opened end of first end 126.

In use, a medication formulation as for example, a gelcap, is inserted into medication reservoir 112. Closing means 110 is twisted onto second end 128 thereby pushing the gelcap against hollow piercing means 118 through which the contents of the gelcap are expressed into nipple chamber 120 wherein they remain until the device is placed into the mouth of an infant or patient. Mouth guard 114 is fixed to the device so as to prevent the patient or infant from swallowing it.

Gelcaps are known in the pharmaceutical arts and comprise medication which has been gelatin encapsulated thereby providing a convenient and accurate formulation for dispensing medication. Special formulations of medications, preferably, but not limited to those used routinely in pediatric care, can be manufactured in gelcap formulation especially suited for use in the present invention.

Referring now to FIGS. 8–11 wherein similar reference characters designate corresponding parts throughout the several views, a further embodiment of the present invention is illustrated.

Pierced nipple 216 has nipple chamber 220 and open base 222 with circumferential nipple flange 240. Medication reservoir 212 has outer wall member defining reservoir chamber 232 having a volume fixed to be less than that of a formulation of a medication, as for example a gelcap 244. There is first end 226 opening into reservoir chamber 232, and closable second end 228 also opening into reservoir chamber 232. Closable second end 228 is of sufficient dimensions to receive a medication formulation, her gelcap 244. First end 226 communicates with nipple chamber 120 through strainer 213 which is fixed to first end 226.

There is means 230 for firmly engaging reservoir 212 to base 222 of nipple 216 in fluid-tight relationship. Strainer 213 is shown as a useful engaging means. Bas 222 of nipple 216 is sealingly forced against the reservoir 212 at first end 226 around the opening in the first end. Circumferential nipple flange 240 is forced against the first end 226 of reservoir 212 by strainer 213 which is snapped down over base 222. Other useful engaging means can be used such as the means illustrated in the various embodiments of the present invention presented herein.

Mouthguard 214 is fixed to the device at a position which is preferably proximal to first end 226 of reservoir 212 and distal to closable second end 128 of reservoir 212. The mouthguard 214 shown here is a commonly molded extension near the opened end of first end 126.

Closing means 210 is operable to seal second end 228 of reservoir 212. The closing means has associated therewith a means to extend into and decrease the volume of reservoir chamber 232 as the closing means closes the second end 212. The closing means can be a cap 210 which screws into the second end 228 of reservoir 212. Preferably a seal is formed at the interface 246 of the contacting surface between closing means 210 and closable second end 228 when the cap 210 is in a closed position.

Medication reservoir 212 has interior wall 215 from which extends at least one piercing means 219. Here, three piercing means 219 extend into reservoir 212 from closing means 210 the interior surface of which forms part of interior wall 215 of medication reservoir 212.

In use, a medication formulation as for example, a gelcap is inserted into medication reservoir 212. Closing means 210 is twisted onto second end 228 thereby pushing piercing means 219 into the gelcap. The contents of the gelcap remain in reservoir 212 until use when they pass through strainer 113 into nipple chamber 220. Strainer 213 prevents pieces of the pierced gelcap from entering nipple chamber 220.

The present invention includes a method for the oral administration of a medication to a patient with a device which comprises a pierced nipple having a nipple chamber and an open base, a medication reservoir having an outer wall member defining a hollow reservoir chamber, a first end opening into the reservoir chamber and communicating with the nipple chamber, and a closable second end opening into the reservoir chamber; means disposed on the first end for firmly engaging the base of the nipple in fluid-tight relationship; and closing means operable to seal the second end of the reservoir. The method comprises the steps of adding a medication formulation to the reservoir, and administering the medication to the patient through the nipple.

Alternatively, the present invention includes a method for the oral administration of a medication to a patient with a device which comprises a pierced nipple having a nipple chamber and an open base, a medication reservoir having an outer wall member defining a reservoir chamber of fixed volume, a first end opening into the reservoir chamber, and a closable second end opening into the reservoir chamber, the closable second end being of dimensions sufficient to receive a medication formulation, a hollow piercing means fixed to the first end and protruding into the reservoir chamber, through which the first end communicates with the nipple chamber, means disposed on the first end for firmly engaging the base of the nipple in fluid-tight relationship, and closing means operable to seal the second end of the reservoir.

The method comprises the steps of inserting a gelcap formulation of a medication into the medication reservoir, closing the reservoir, the action of which forces the piercing means into the gelcap, thereby expressing its contents through the piercing means into the reservoir and administering the medication to the patient through the nipple.

What is claimed is:

1. A device for the oral administration of a medication which comprises:

a pierced nipple having a nipple chamber and an open base, a medication reservoir having an outer wall member defining a reservoir chamber, a first end opening into the reservoir chamber, and a closable second end opening into the reservoir chamber, means to connect the first end of the reservoir to the open base of the nipple in fluid-tight relationship with the nipple chamber communicating with the reservoir chamber through a strainer, and closing means operable to seal the second end of the reservoir.

2. The device according to claim 1 which further comprises a mouth guard fixed to the device in a position proximal to the first end of the reservoir and distal to the closable second end of the reservoir.

3. The device according to claim 1 in which the closable second end is of dimensions sufficient to receive a medication formulation.

4. A device for the oral administration of a medication which comprises:

a pierced nipple having a nipple chamber and an open base, a medication reservoir having an outer wall member defining a reservoir chamber, a first end opening into the reservoir chamber, a closable second end opening into the reservoir chamber, and an interior wall from which extends at least one piercing means, means to connect the first end of the reservoir to the open base of the nipple in fluid-tight relationship with the nipple chamber communicating with the reservoir chamber through the open base, and closing means operable to seal the second end of the reservoir.

5. The device according to claim 4 which further comprises a mouth guard fixed to the device in a position proximal to the first end of the reservoir and distal to the closable second end of the reservoir.

6. The device according to claim 4 in which the closable second end is of dimensions sufficient to receive a medication formulation.

7. A device for the oral administration of a medication which comprises:

a pierced nipple having a nipple chamber and an open base, a medication reservoir having an outer wall member defining a reservoir chamber, a first end opening into the reservoir chamber, and a closable second end opening into the reservoir chamber, means to connect the first end of the reservoir to the open base of the nipple in fluid-tight relationship with the nipple chamber communicating with the reservoir chamber through the open base, and closing means operable to seal the second end of the reservoir with at least one piercing means extending into the reservoir chamber from the closing means.

8. The device according to claim 7 which further comprises a mouth guard fixed to the device in a position proximal to the first end of the reservoir and distal to the closable second end of the reservoir.

9. The device according to claim 7 in which the closable second end is of dimensions sufficient to receive a medication formulation.

10. The device according to claim 7 wherein the closing means further comprise means operable to decrease the volume of the reservoir chamber as the closing means closes.

11. A device for the oral administration of a medication which comprises:

a pierced nipple having a nipple chamber and an open base, a medication reservoir having an outer wall member defining a reservoir chamber of fixed volume, a first end opening into the reservoir chamber, and a closable second end opening into the reservoir chamber, the closable second end being of dimensions sufficient to receive a medication formulation, a hollow piercing means through which the first end communicates with the nipple chamber, said piercing means fixed to the first end and protruding into the reservoir chamber, means disposed on the first end for firmly engaging the base of the nipple in fluid-tight relationship, and closing means operable to seal the second end of the reservoir.

12. The device according to claim 11 which further comprises a mouth guard fixed to the device in a position proximal to the first end of the reservoir and distal to the closable second end of the reservoir.

13. The device according to claim 11 in which said closing means comprises a child safety cap.

14. A method for the oral administration of a medication comprising the steps of:

inserting a gelcap comprising a medication into a reservoir chamber of a medication reservoir having a first chamber opening, a second chamber opening, and a gelcap piercing means, the medication reservoir being connected to a pierced nipple through the first chamber opening and communicating with the nipple, the gelcap being inserted into the reservoir chamber through the second chamber opening;

closing the second chamber opening of the reservoir;

piercing the gelcap with the gelcap piercing means by the action of closing the reservoir to enable the medication to release from the gelcap into the reservoir; and administering the medication to the patient from the reservoir through the pierced nipple.

* * * * *